US012329482B2

(12) United States Patent
Chauhan

(10) Patent No.: US 12,329,482 B2
(45) Date of Patent: Jun. 17, 2025

(54) MOTORIZED SURGICAL SYSTEM FOR POSITIONING AND ALIGNMENT OF SURGICAL INSTRUMENTS

(71) Applicant: Sunita Chauhan, Malvern East (AU)

(72) Inventor: Sunita Chauhan, Malvern East (AU)

(*) Notice: Subject to any disclaimer, the term of this patent is extended or adjusted under 35 U.S.C. 154(b) by 1021 days.

(21) Appl. No.: 17/059,114

(22) PCT Filed: May 17, 2019

(86) PCT No.: PCT/AU2019/050478
§ 371 (c)(1),
(2) Date: Nov. 25, 2020

(87) PCT Pub. No.: WO2019/227129
PCT Pub. Date: Dec. 5, 2019

(65) Prior Publication Data
US 2021/0369388 A1     Dec. 2, 2021

(30) Foreign Application Priority Data

May 29, 2018  (AU) ................. 2018901888

(51) Int. Cl.
*A61B 90/11*   (2016.01)
*A61B 1/00*    (2006.01)
(Continued)

(52) U.S. Cl.
CPC .......... *A61B 34/37* (2016.02); *A61B 1/00147* (2013.01); *A61B 90/11* (2016.02); *A61B 90/50* (2016.02)

(58) Field of Classification Search
CPC ..... A61B 90/11; A61B 90/57; A61B 1/00147; A61B 2090/571
See application file for complete search history.

(56) References Cited

U.S. PATENT DOCUMENTS 6,110,182 A  *  8/2000  Mowlai-Ashtiani ... A61B 90/11
                                                        606/1
6,283,977 B1 *  9/2001  Ericsson ............... A61B 90/10
                                                        606/130
(Continued)

FOREIGN PATENT DOCUMENTS

DE  102013111935 A1 *  4/2015  ............. A61B 90/50
EP      1681029 A1 *  7/2006  ............. A61B 90/11
(Continued)

OTHER PUBLICATIONS

International Search Report prepared by the Australian Patent Office for PCT/AU2019/050478, Jul. 17, 2019, 4 pages.
(Continued)

*Primary Examiner* — Martin T Ton
(74) *Attorney, Agent, or Firm* — Portland IP, LLC; Abdullah O. Alnajran

(57) ABSTRACT

An instrument carrier for assisting with the positioning of a surgical instrument during surgery, the carrier having an arcuate rail mountable to an operating table and moveable relative to the table for positioning the rail over a target region in use; and a carriage operatively coupled to the rail, the carriage having a support for carrying the surgical instrument; where the carriage is configured to be movable along the rail such that movement of the carriage positions the surgical instrument along an arcuate path relative to the target region.

13 Claims, 18 Drawing Sheets

(51) Int. Cl.
   *A61B 34/37*     (2016.01)
   *A61B 90/50*     (2016.01)

(56)         References Cited

U.S. PATENT DOCUMENTS

2002/0007188 A1*  1/2002  Arambula ........... A61B 17/1757
                                                        606/130
2014/0249546 A1*  9/2014  Shvartsberg ........... B25J 9/0084
                                                        606/130
2017/0232229 A1*  8/2017  Flores ............... A61M 25/0097
                                                        604/506
2018/0279992 A1* 10/2018  Frankel ................ A61G 13/101
2019/0223967 A1*  7/2019  Abbott ................... A61B 34/30

FOREIGN PATENT DOCUMENTS

EP          2893898 B1        3/2017
KR          20200012516 A  *  2/2020  ......... A61B 1/00147
WO       WO-2013057207 A1  *  4/2013  ......... A61B 1/00009
WO          2013/078529 A1    6/2013
WO          2017/059343 A1    4/2017

OTHER PUBLICATIONS

Written Opinion prepared by the Australian Patent Office for PCT/AU2019/050478, Jul. 17, 2019, 5 pages.

* cited by examiner

MOTORIZED SURGICAL SYSTEM FOR POSITIONING AND ALIGNMENT OF SURGICAL INSTRUMENTS

The invention relates to a surgical system and in particular to a motorised robotic surgical system for assisting with the positioning and alignment of surgical instruments during surgery.

Minimally Invasive Surgery (MIS) has become the gold standard for many operative interventions in both paediatric and adult patient populations. MIS procedures such as laparoscopic operations are performed by introducing surgical instruments through a small incision with their trajectory of motion being guided by real-time feedback on a computer display. MIS has been proven to confer several advantages over open conventional surgery, such as optimum access wounds, reduced trauma, faster recovery, reduced hospitalisation time and post-operation complications—substantially improving the cost-effectiveness of surgical procedures for the hospital and the society in general.

Conventional robotic and instrument positioning systems for performing MIS are based on anthropometric (or human-arm like) configurations, for example anthropometric configurations with added/modified features such as multiple (more than two) arms or arms with more/less than 6 DOFs and as described in PCT publication WO 2000/07503. However, the applicant has identified that surgeons using such anthropometric systems are often faced with the problem of unwanted tremors and inaccuracies, such as dynamic bending beam effects; massive foot-prints; fulcrum effect etc, when adjusting the position of conventional surgical instrument positioning systems carrying long and slender instruments. Additionally, the conventional anthropometric instrument positioning systems must travel large distances even for small angular movement adjustments, therefore rendering such systems unsuitable for performing surgery on smaller patients such as toddlers and infants.

The applicant has determined that it would be advantageous to provide an instrument carrier and surgical system for performing procedures on both paediatric and neonatal patients while retaining the same advantages for adult patients as well. The present invention seeks to at least in part alleviate the problems identified above.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

According to an aspect of the present invention, there is provided an instrument carrier for assisting with the positioning of a surgical instrument during surgery, comprising: an arcuate rail mountable to an operating table and moveable relative to the table for positioning the rail over a target region in use; and a carriage operatively coupled to the rail, the carriage having a support for carrying the surgical instrument; wherein the carriage is configured to be movable along the rail such that movement of the carriage positions the surgical instrument along an arcuate path relative to the target region.

Preferably, the rail is motorised to pivot relative to the table about a mounting end of the rail, and the carriage is motorised to move along the rail.

Preferably, movement of the carrier and the instrument is remotely controlled.

Preferably, the support comprises a ball joint having a central cavity for receiving a surgical instrument. Preferably, a shaft for receiving a surgical instrument is axially located within the ball joint and movable relative to the ball joint by a rack and pinion drive.

Preferably, the support is configured to receive surgical instruments having a diameter of 5 mm or less.

Preferably, the rail extends substantially only half way across a width of an operating table. Preferably, the carrier is adapted to be joined to an opposing like carrier to form a unitary rail which extends across substantially the entire width of an operating table. Alternatively, the rail extends across substantially the entire width of an operating table.

Preferably, the support is adapted to carry an endoscopic or laparoscopic instrument.

According to another aspect of the present invention, there is provided a motorised surgical system for use in positioning surgical instruments during surgery, comprising:
 a guide mountable to a operating table such that it extends along a side of the operating table in use;
 an instrument carrier for positioning a surgical instrument during surgery, comprising an arcuate rail mountable to the guide and moveable relative to the table for positioning the rail over a target region in use, and a carriage operatively coupled to the rail, the carriage having a support for carrying the surgical instrument, wherein the carriage is configured to be movable along the rail such that movement of the carriage positions the surgical instrument along an arcuate path relative to the target region;
 a first driver associated with the carriage and adapted to move the carriage along the rail, a second driver associated with the carrier and adapted to move the rail in a swinging motion relative to the table, and a third driver associated with the guide and adapted to move the rail along the guide relative to the table; and
 a controller configured to receive directional input for an end point of the surgical instrument, compute corresponding movement required by the drivers and provide output signal to actuate the drivers based on the input.

Preferably, the system further comprises a second guide positioned to extend along an opposing side of the table for supporting same/or an additional instrument carrier.

Preferably, comprising a further guide positioned along the same side of the table as the first mentioned guide and adapted for supporting an additional instrument carrier.

Preferably, the guide is located along a longitudinal length of the table.

Preferably, the, or, each guide is detachably coupled to the table.

Preferably, the instrument carrier comprises a second arcuate rail, wherein one of the rail is of substantially semi-circular extend, and the other rail extends only substantially a quadrant of a circle.

According to another aspect of the present invention, there is provided an apparatus for use in supporting an instrument carrier, comprising a guide mountable to a work surface such that it extends along a side of the work surface in use, the guide comprises one or more tracks extending in a longitudinal direction and adapted for supporting and moving the instrument carrier along the track.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

The invention will now be described, by way of example only, with reference to the accompanying drawings, in which.

Figure 1:
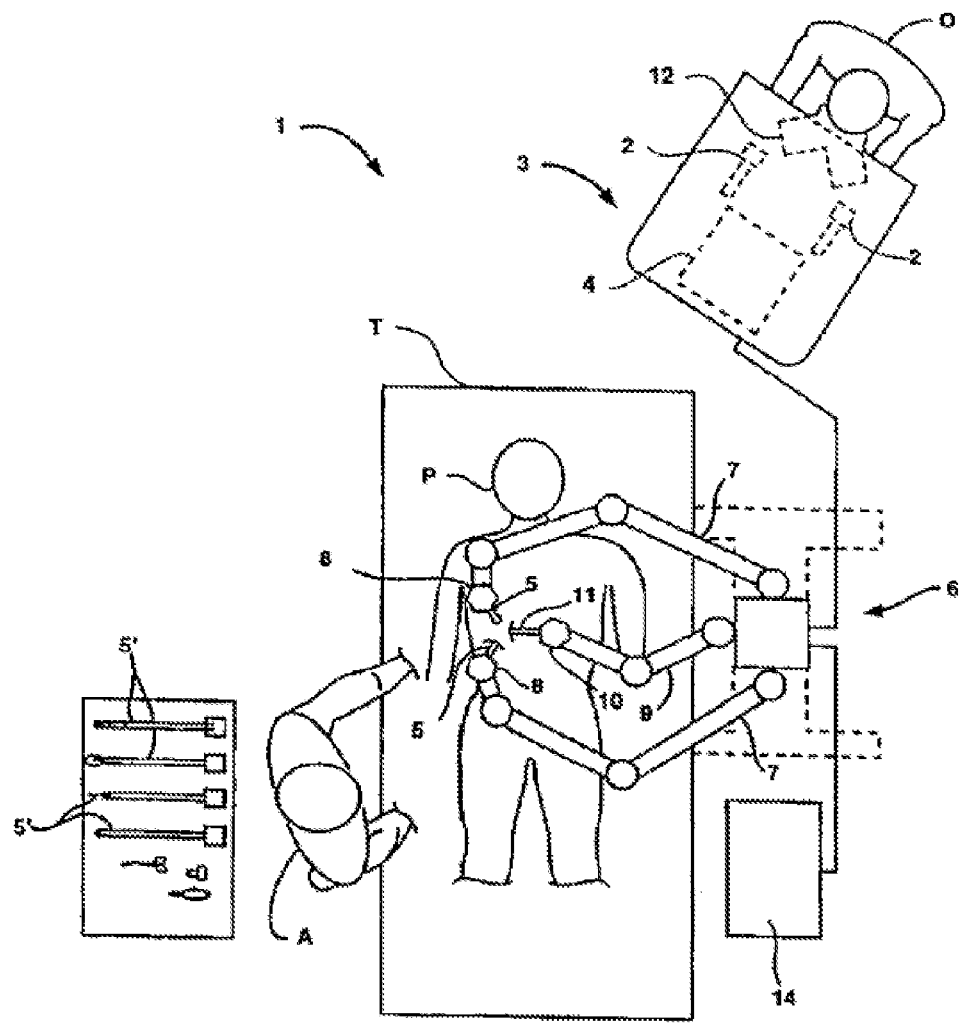
FIG. 1 is a schematic plan view of a robotic surgical system performing a minimally invasive surgical procedure as described in WO2000/07503.
Figure 2:
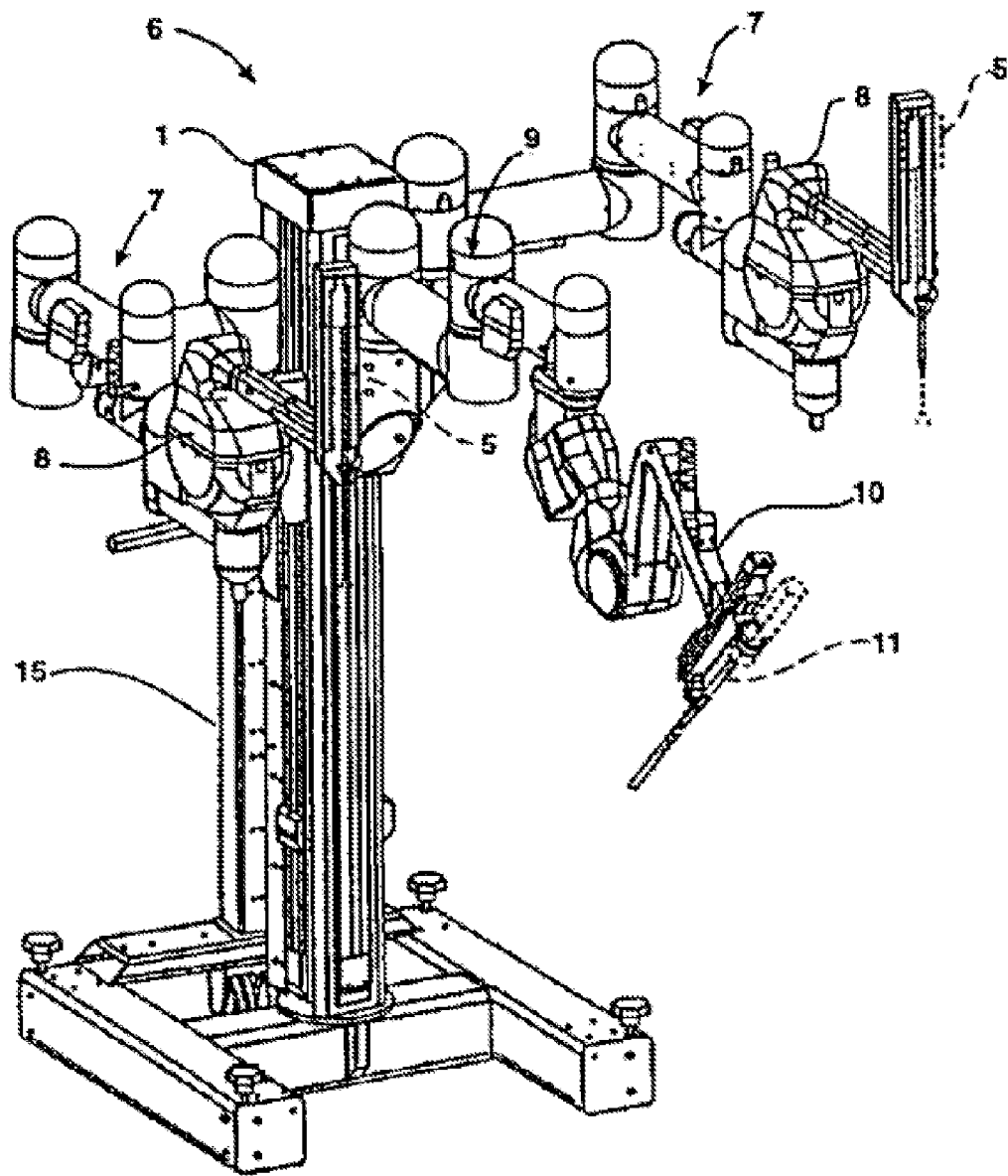
FIG. 2 is a perspective view of the robotic arms of the system described in FIG. 1.

FIG. 1 shows a schematic plan view of a conventional robotic surgical system performing a minimally invasive robotic surgical procedure as described in PCT publication WO 00/07503. An operator (usually a surgeon) is shown performing surgery on a patient remotely using a "master-slave" robotic system, where the movements of instrument carriers, in the form of robotic arms, are controlled by the operator. FIG. 2 shows a perspective view of the robotic arms where the surgical instruments are held by anthropometric arm-like configurations.

Figure 3:
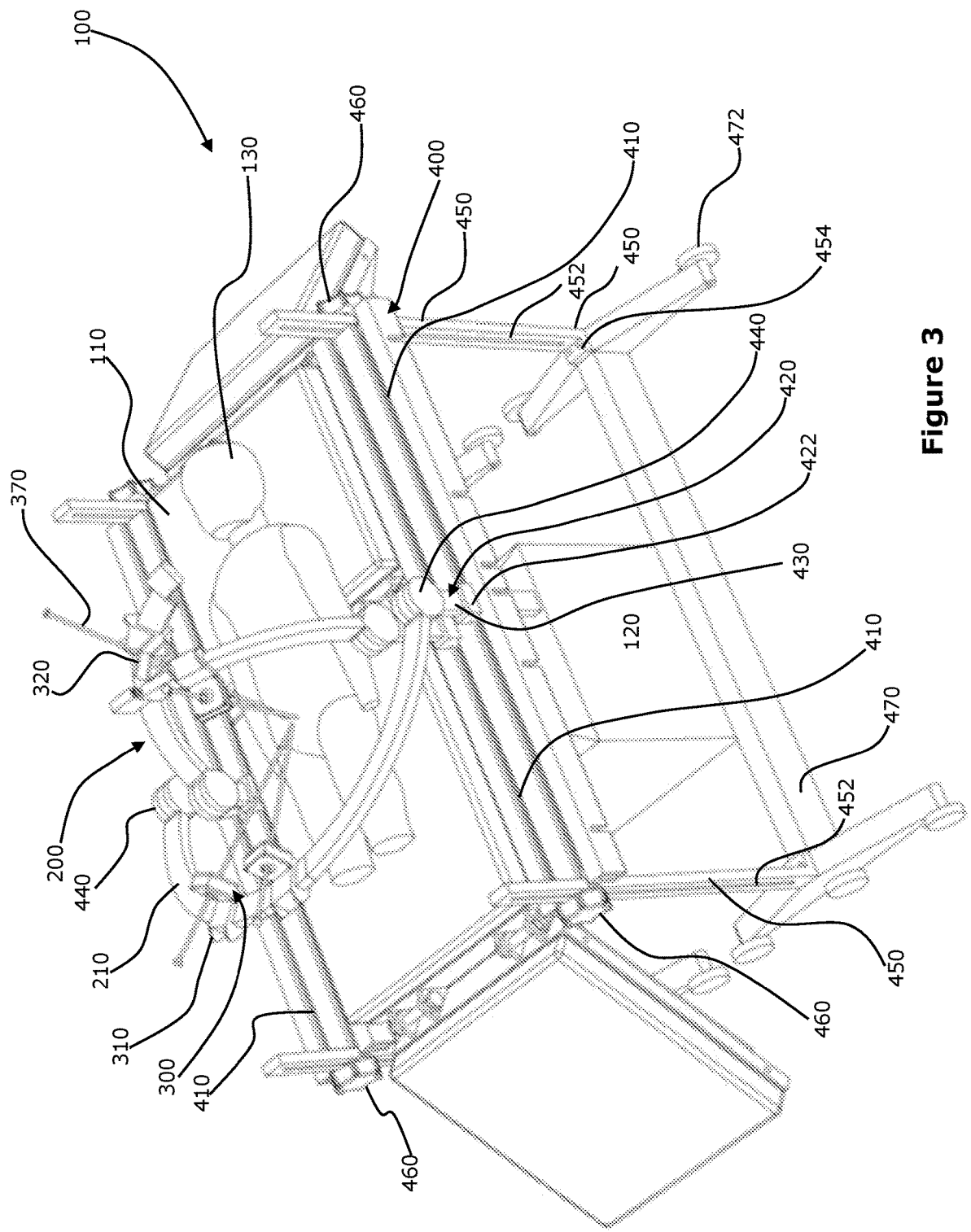
FIG. 3 is a perspective view showing an instrument positioning system according to an embodiment of the present invention.
Figure 4:
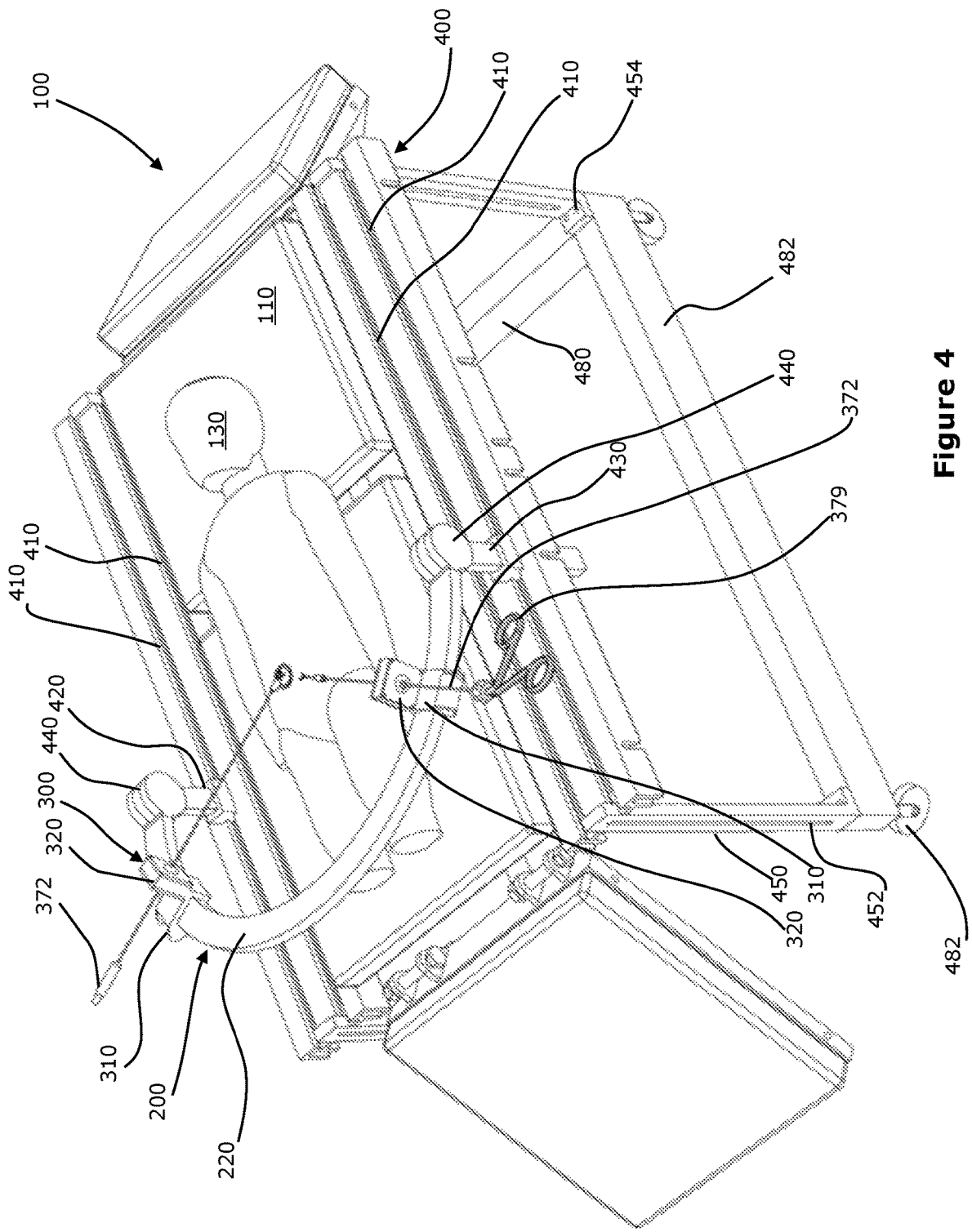
FIG. 4 is a perspective view showing an instrument positioning system according to another embodiment of the present invention.

FIGS. 3 and 4 show a surgical system 100 in accordance with an embodiment of the present invention. The surgical system 100 comprises one or more instrument carriers 200 having an instrument carriage 300 movable along the carrier 200 for holding and assisting with the positioning of a surgical instrument during surgery. The instrument carrier 200 is mountably supported on a guide 400 that can be coupled to the sides of a surgical workspace in the form of an operating table 110 for positioning surgical instruments 370 relative to the operating table 110 in use. The operating table 110 can be a standard operating table suitable for performing surgical operating, including paediatric or neonatal surgical procedures.

More specifically, with reference to FIGS. 5 to 8, the instrument carrier 200 comprises an elongated rail member 210. The rail 210 is of arcuate form. In another configuration, the rail can have a linear-extending portion. The rail 210 is shown to have a rectangular cross-section, however, it is to be understood that the rail 210 could also have a circular, oval or any other suitable cross-section. In one embodiment, the rail 210 extends in length that is substantially only half way across a width of the operating table 110 and is in the form of a quadrant. In another embodiment, the rail 210 extends in length across substantially the entire width of the operating 110 and taking a semi-circular form. The rail 210 has a mounting end 212 for coupling to a mounting member 440. In use, the rail 210 is mounted to the mounting member 440 and the guide 400 such that the instrument carrier 200 is oriented in an upward direction (to be described further below). One or more carriages 300, adapted for carrying surgical instruments 370, is configured to be retained on the rail 210 and movable along the rail 210 (to be described further below).

Figure 5:
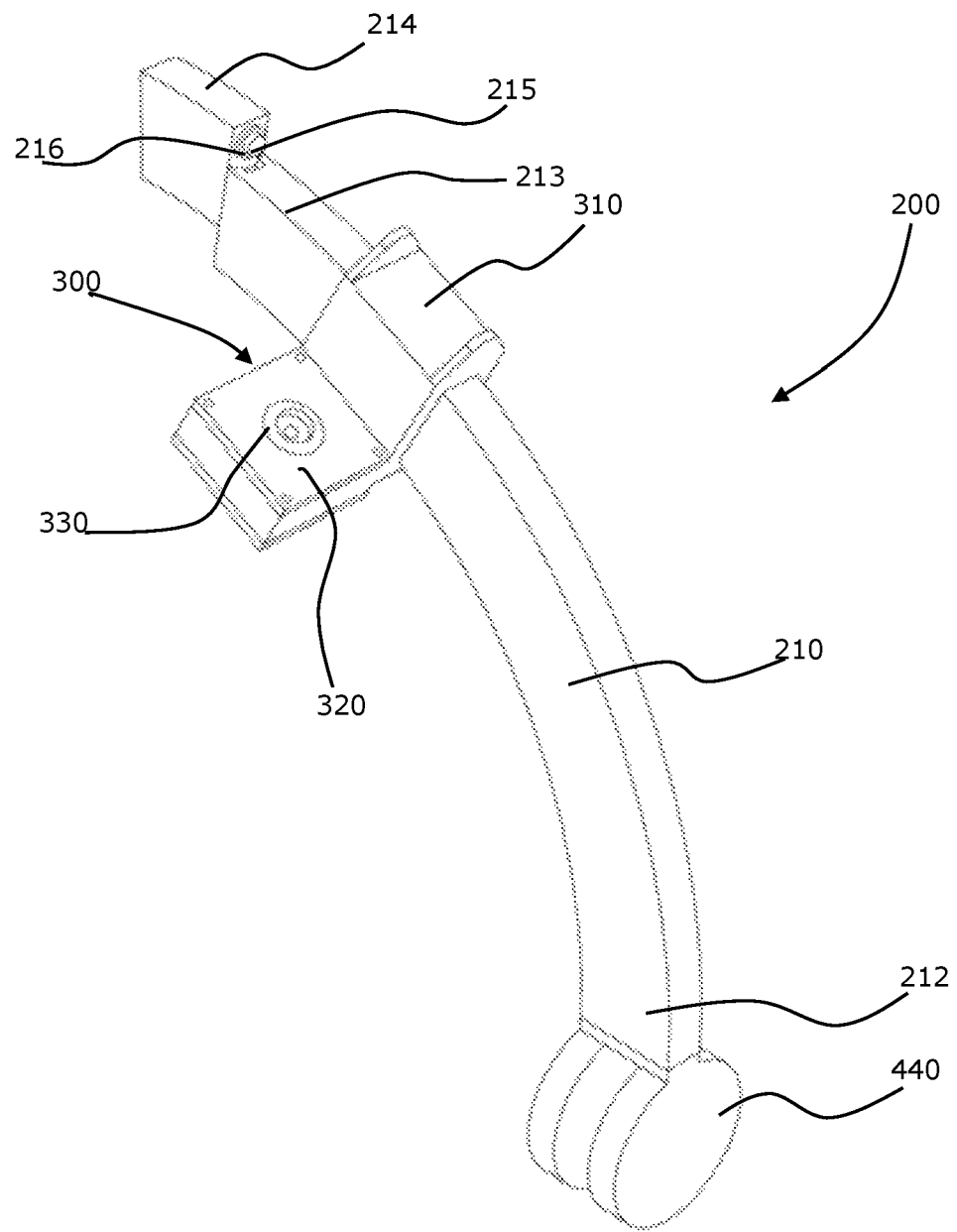
FIG. 5 is a perspective view showing an instrument carrier according to an embodiment of the present invention.
Figure 6:
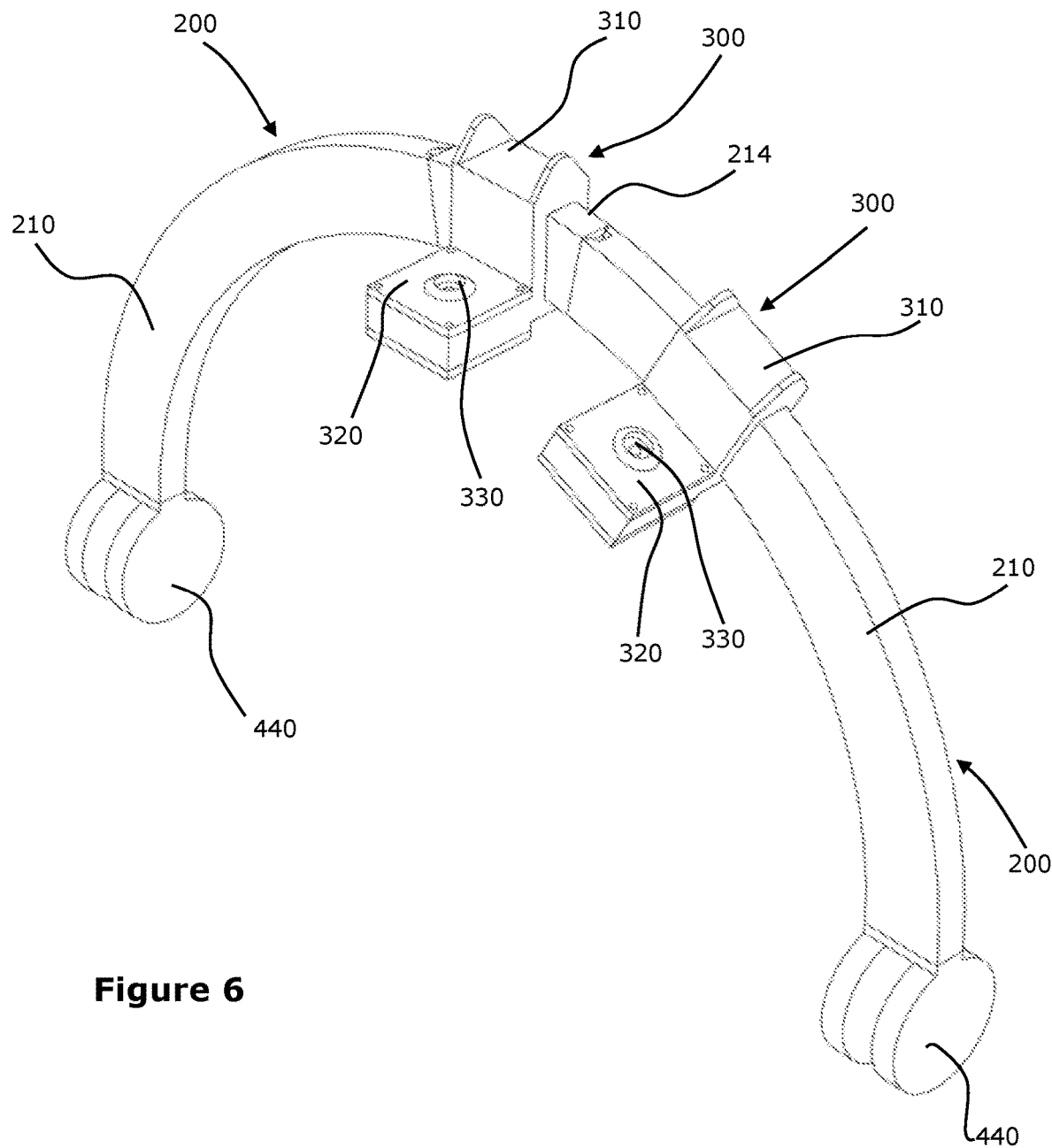
FIG. 6 is a perspective view showing an instrument carrier according to another embodiment of the present invention.
Figure 7:
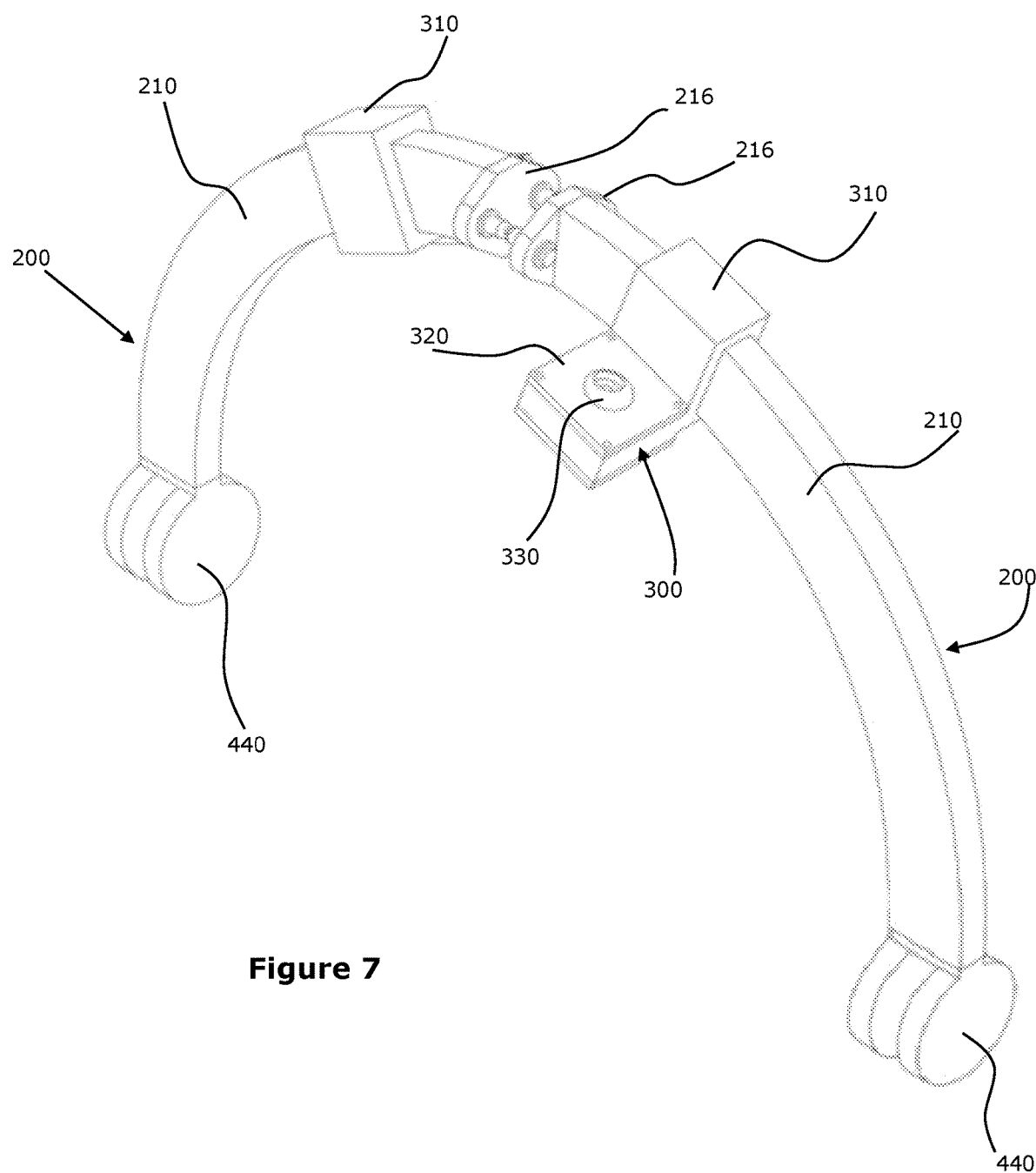
FIG. 7 is a perspective view showing an instrument carrier according to another embodiment of the present invention.

Referring to FIG. 5, the quadrant form of the rail 210 has an end portion 213 opposite the mounting end 212. The end portion 213 comprises a recess 216 capable of detachably coupling with an end stop 214. The end stop 214 can be slidably coupled to the recess 216 and movable between a first position in which the end stop 214 forms a raised portion proximate the end portion 213 and a second position in which the end stop 214 is flush against the rail 210. The first configuration advantageously prevents the movement of the carriage 300 from travelling beyond the end portion 213 of the rail 210. The end stop 214 can also have a protrusion 215 extending from its rail-facing side for abutting the carriage 300 in use. The end stop 214 can be used to join two like-rails 210 in the quadrant form to form a unified semi-circular rail. For example, as illustrated in FIG. 6, the quadrant rails 210 can be configured to join together, to allow carriage(s) 300 to freely move between the quadrant rails 210, in an end-to-end arrangement with the end stop 214 in its second position and acting as a locking member between the rails 210. This advantageously demonstrates the flexibility of the quadrant rails 210 being able to be configured in either individual quadrant form or joined together in a semi-circular form.

In another configuration, the end portion 213 of the rail 210 is provided with a flange 218 to prevent the movement of the carriage 300 from travelling beyond the end portion 213 of the rail 210. The flange 218 may have protrusion(s) extending from its rail-facing side for abutting the carriage 300 in use.

Figure 8:
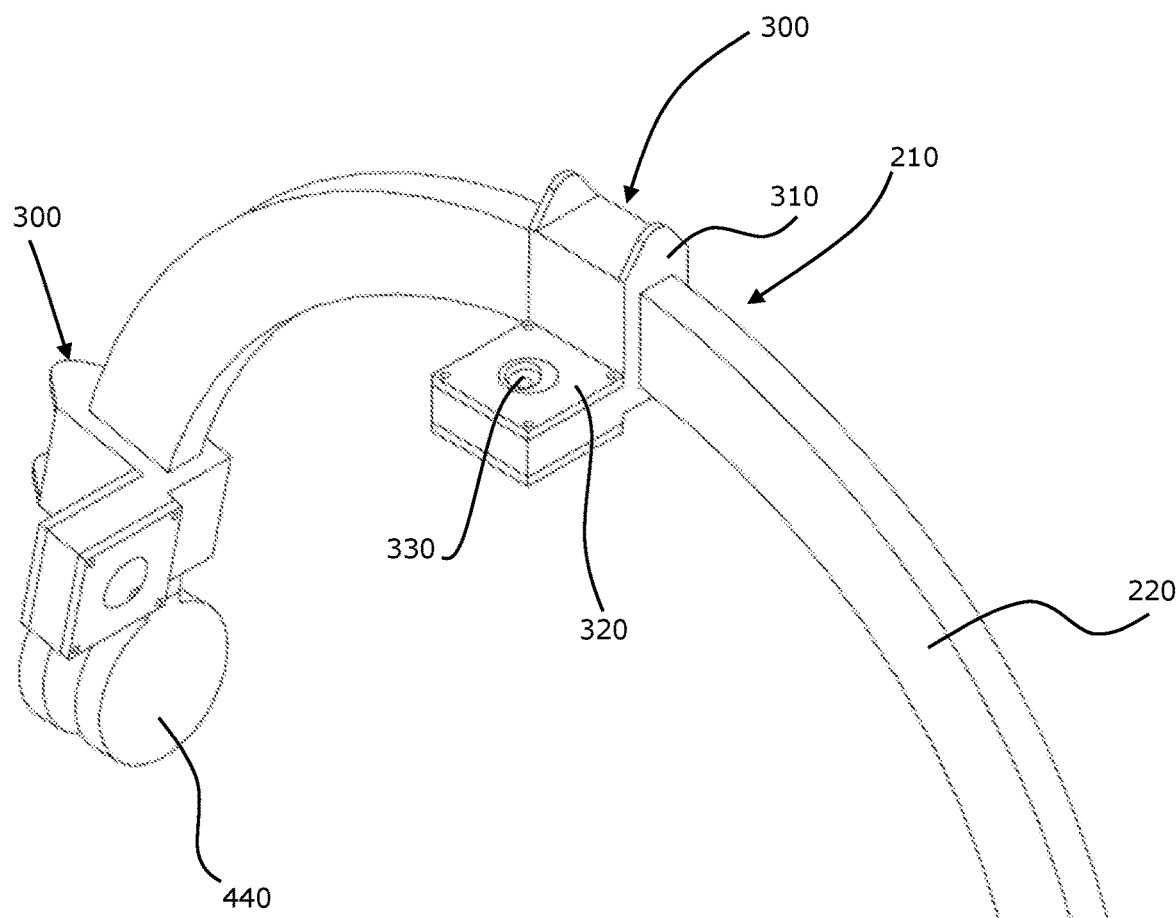
FIG. 8 is a perspective view showing an instrument carrier according to another embodiment of the present invention.

FIG. 8 shows the instrument carrier 200 having a single elongated rail member 220 in the form of a semi-circle. The semi-circular rail 220 has two mounting ends 222 for coupling to respective mounting members 440. One or more carriages 300 are adapted to move freely along the rail 220.

Figure 9:
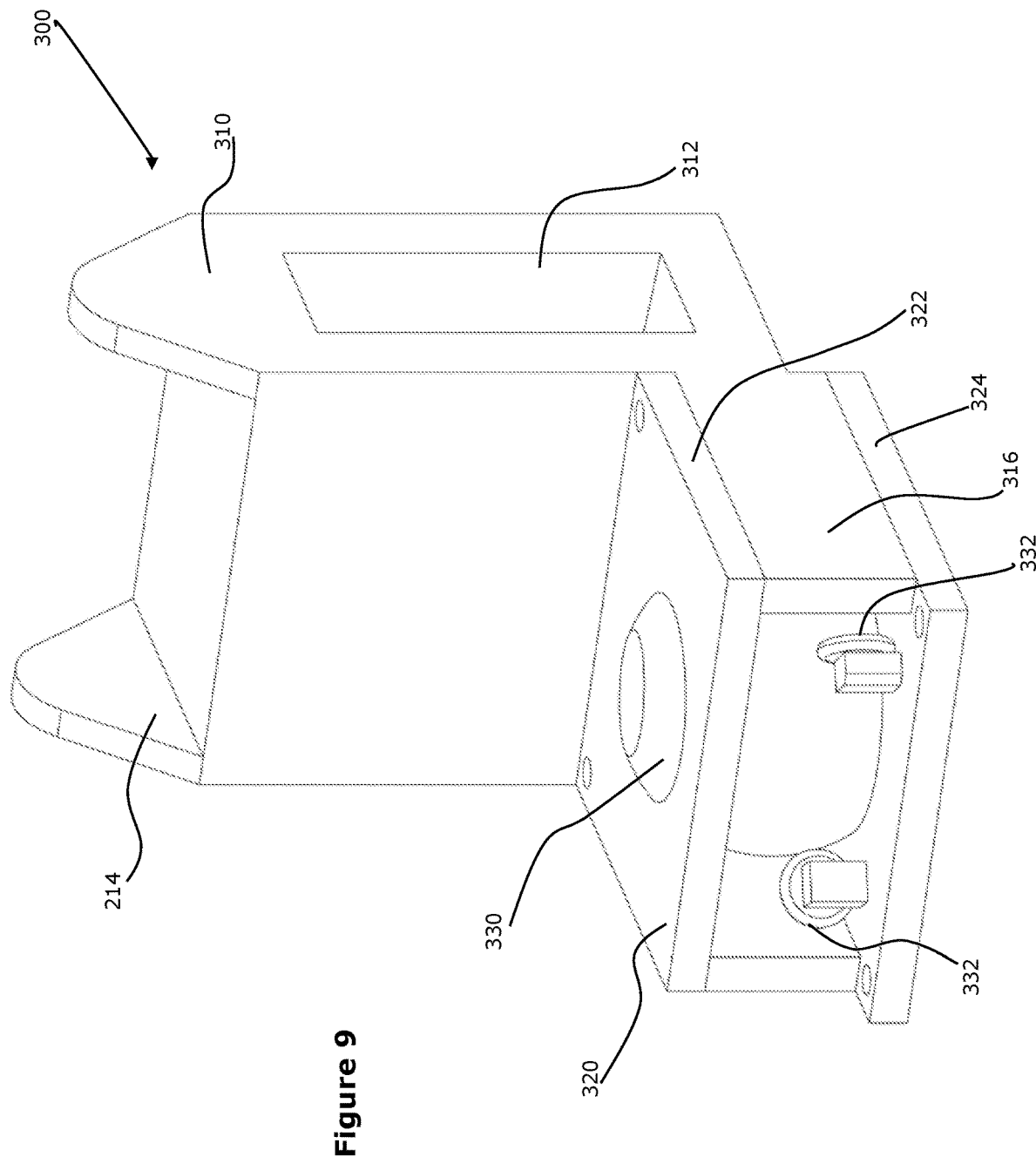
FIG. 9 is a perspective view showing an instrument carriage according to an embodiment of the present invention.
Figure 10:
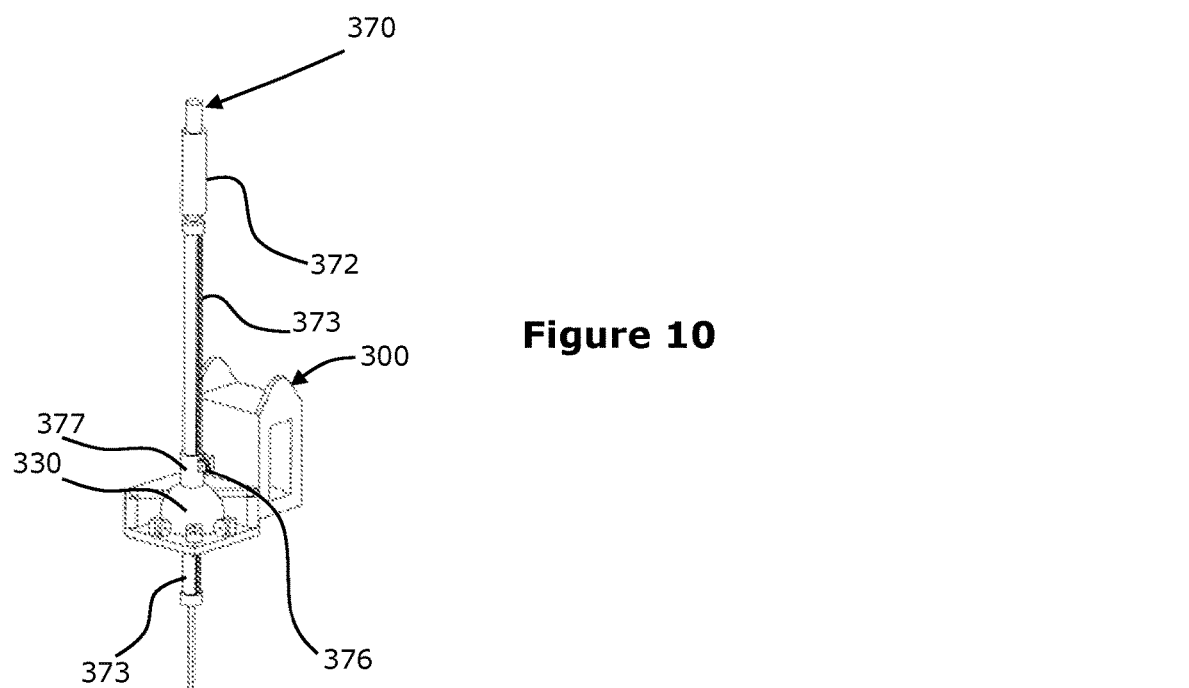
FIG. 10 is a perspective view showing an instrument carriage coupled with a surgical instrument according to another embodiment of the present invention.
Figure 11:
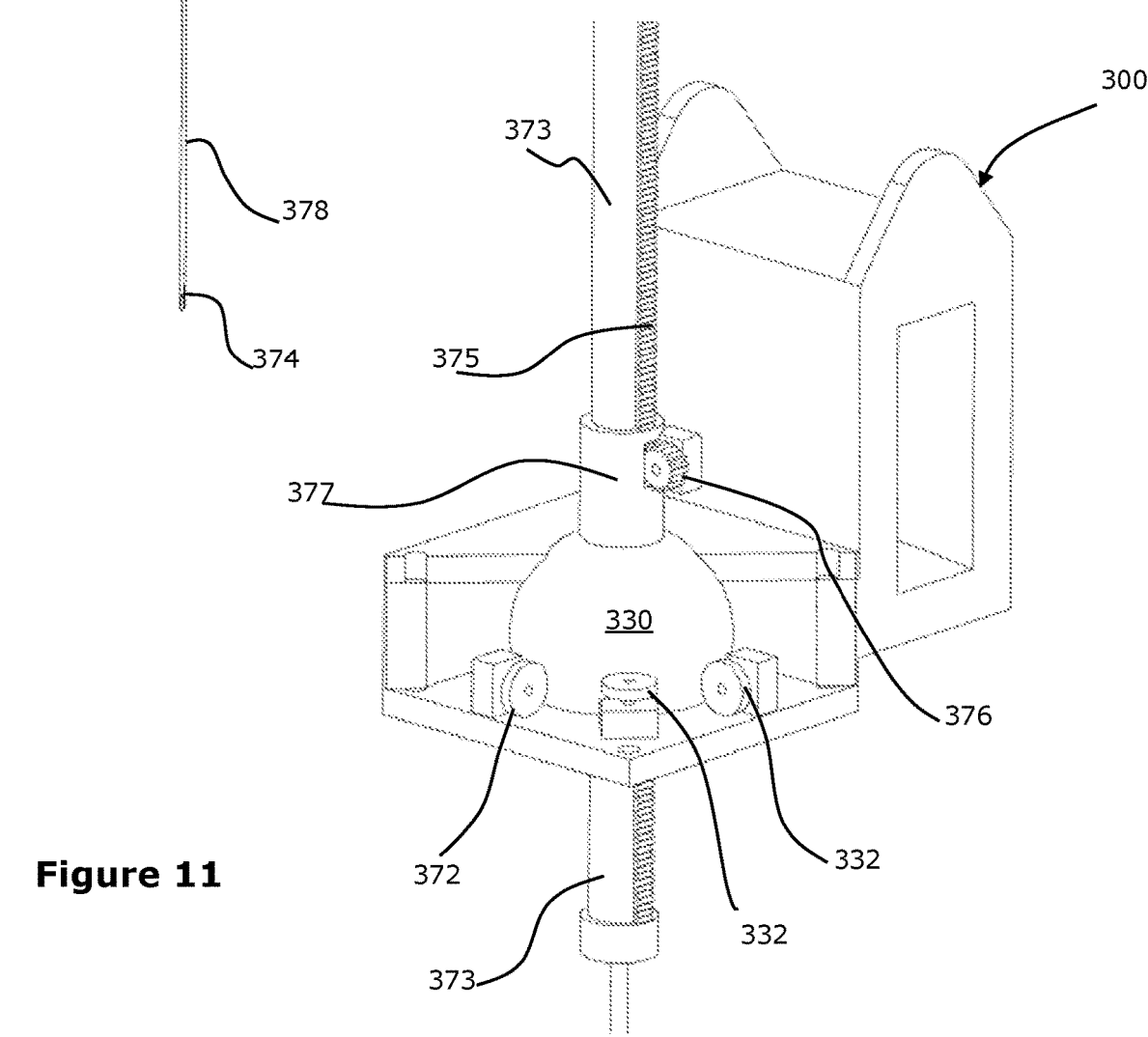
FIG. 11 is a close up part-sectional perspective view showing the instrument carriage of FIG. 10.
Figure 12:
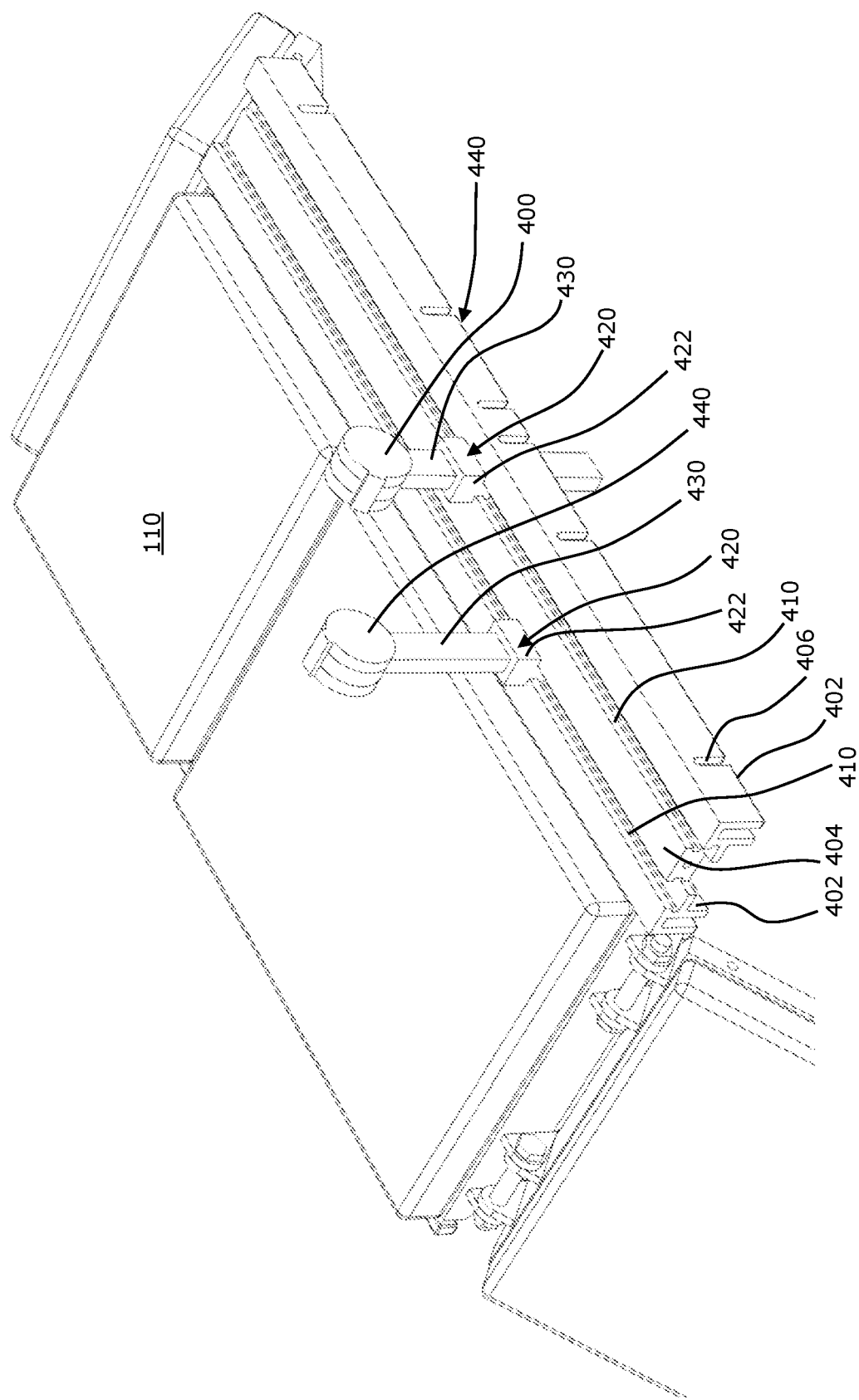
FIG. 12 is a perspective view showing a guide coupled to an operating table according to an embodiment of the present invention.
Figure 13:
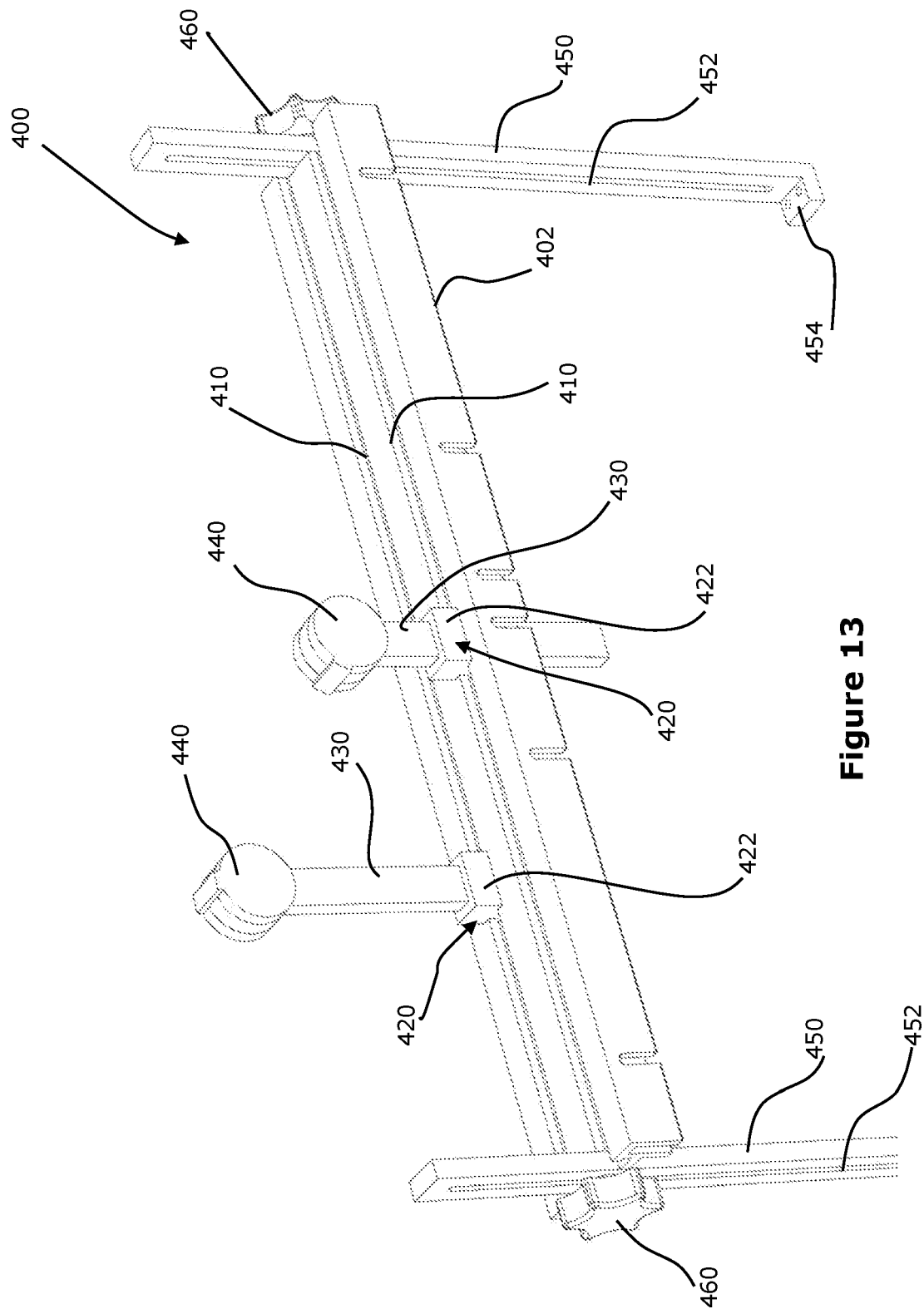
FIG. 13 is a perspective view showing a guide having vertical stands according to an embodiment of the present invention.

Referring to FIGS. 9 to 11, there is shown a preferred embodiment of the carriage 300 for carrying a surgical instrument 370. The carriage 300 is provided with a mounting portion 310 and an instrument support portion 320. The mounting portion 310 has an embedded slot 312 sized and dimensioned to receive the rail 210 so that the carriage can slide along the rail 210. The slot 312 is shown to have a rectangular cross-section, however it is to be appreciated that the shape and dimension of the slot 312 is configured to be complementary to the cross-section shape and dimension of the rail 210, 220. The carriage 300 can be moved manually by force along the rail 210, 220. In one embodiment, the mounting portion 310 of the carriage 300 is fitted with drivers, such as for example one or more motorised wheels (not shown) inside the slot 312, for engaging and moving the carriage 300 along the rail 210, 220, and thereby effecting the movement of any surgical instrument 370 mounted to the carriage 300. The motorised wheel can be controlled remotely by a controller and form part of a robotic surgical system, and the rail 210, 220 can be described as a robotic rail or robotic arc.

A support portion 320 adapted for carrying a surgical instrument 370 extends transversely from the mounting portion 310. Non-limiting examples of the surgical instrument 370 include an endoscopic or laparoscopic instrument. The support portion comprises top plate 322, bottom plate 324 and side walls 316, which together define a housing for holding an instrument support 330. The instrument support 330 is preferably in the form of a ball joint having a central cavity for wholly receiving a shaft of the surgical instrument 370. The ball joint support 330 advantageously provides the surgical instrument 370 with omni-directional movement as the joint is movable with three degrees of freedom. The instrument 370 may be received by the ball joint support 330 and held by friction or interference fit. The instrument 370, when coupled to the ball joint support 330 as described above, can be moved manually by force. In another embodiment, the ball joint support 330 is fitted with drivers, such as for example one or more motorised wheels 332 adjacent to and in contact with the ball joint support 330, for engaging and rotating the ball joint support 330 and thereby effecting the movement of the surgical instrument 370 coupled to the support 330. The motorised wheel can also be controlled remotely by a controller and form part of a robotic surgical system. Although it is shown that side walls 316 and the mounting portion 310 is moulded together in one piece, in some configurations, the side walls 316 and the mounting portion 310 may be formed separately.

In a further configuration, as shown in FIG. 11, the support 330 is further provided with a neck 377 extending from the central cavity of the ball joint support. A hollow, elongate shaft 373 with openings at both ends for receiving a surgical instrument is coupled to the neck 377 and the ball joint support 330. The shaft 373 is provided with a ratchet 375 configuration along its length and adapted to engage a pinion wheel 376 provided at the neck 377. The shaft 373 and its ratchet and pinion arrangement advantageously allow precise and controlled movements of the instrument 370 (received within the shaft 373) in the vertical direction. Without this arrangement, it would be difficult for a surgeon to precisely control the vertical movement of the instrument through the ball joint. This feature is especially helpful for surgical instruments that do not have telescopic extending abilities. The pinion wheel 376 may also be fitted with drivers and motorised such that the movement of the instrument 370 within the shaft 373 can be controlled remotely and by a controller and form part of a robotic surgical system. It can be appreciated that the support 330 can be adapted to receive instrument of various diameters, for example slender endoscopic instrumentation having 5 mm or 3 mm in diameter can be used.

The support 330 described above is of a ball joint with a central cavity, however, it is to be appreciated that the support may instead be in the form of a robotic hand, clamp or any other support suitable for carrying, gasping or handling a surgical instrument or tool.

Turning to FIGS. 12 to 16, there is shown a guide 400 in the form of a supporting platform for supporting and guiding one or more instrument carriers 200. The guide 400 is not only capable of guiding the instrument carriers 200 as described above, but it is equally suitable for guiding other instrument carriers such as conventional remote centre of motion devices, surgical robotic arms and industrial robotic arms. The guide 400 is operatively coupled to a side of a work surface in the form of an operating table 110 to form a fixed frame of reference between the guide and the operating table 110. In one configuration, the guide 400 is coupled to and extends along a longitudinal side of the operating table 110. It is to be appreciated that the guide 400 could also be coupled to and extend along a transverse side of the operating table 110. The guide 400 may be coupled to the operating table 110 by way of a mechanical lock 490, electromagnetic latch 492 or any other suitable mounting mechanisms for securing the guide 400 to a side frame or rail of the operating table 100. The mechanical lock 490, in the form of a slidable lock, in combination with magnetic forces of the electromagnetic latch 492 securely holds the guide 400 to the operating table 100 and reduces translational movements of the guide 400 during use.

Figure 14:
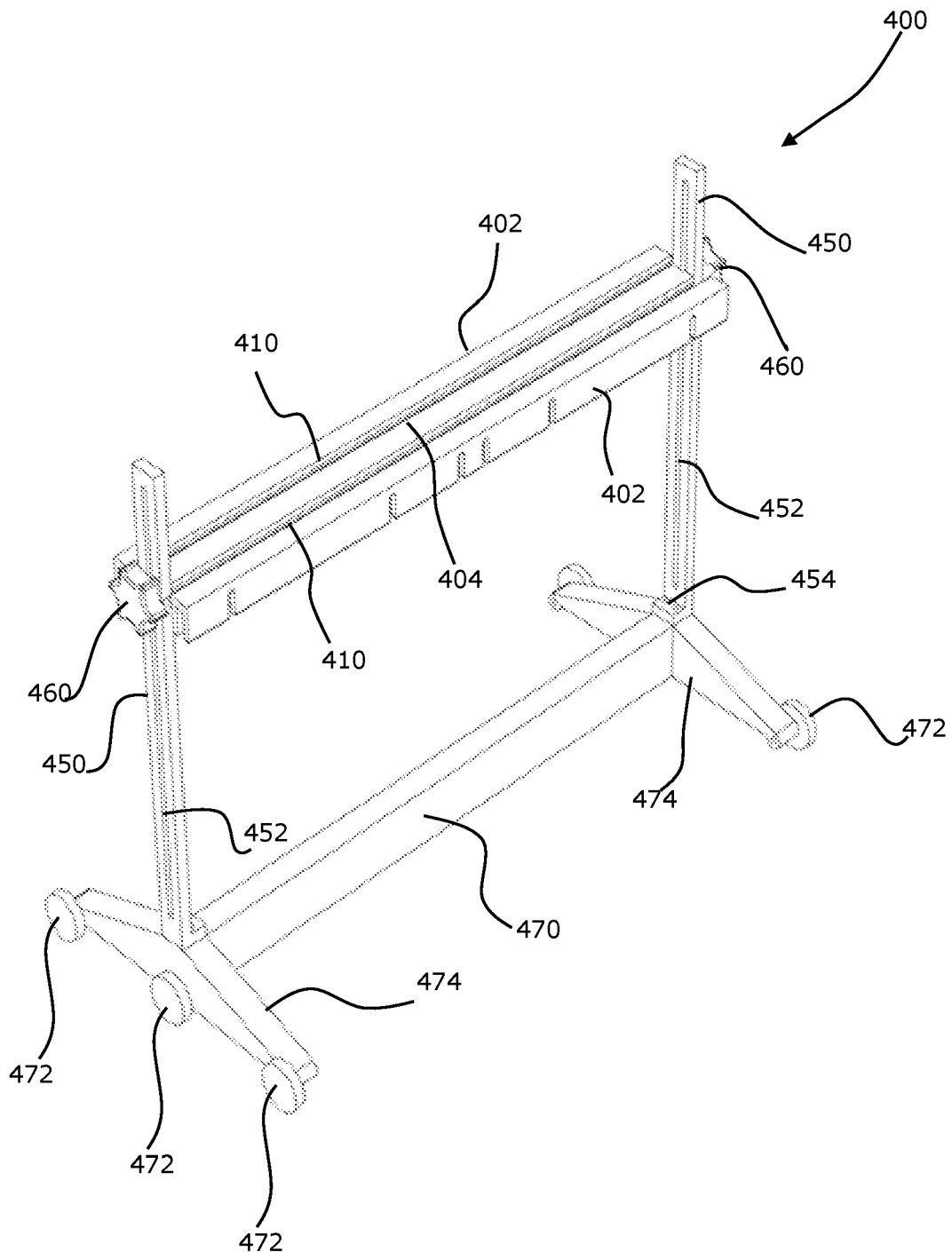
FIG. 14 is a perspective view showing a guide coupled to a wheeled base according to an embodiment of the present invention.
Figure 16:
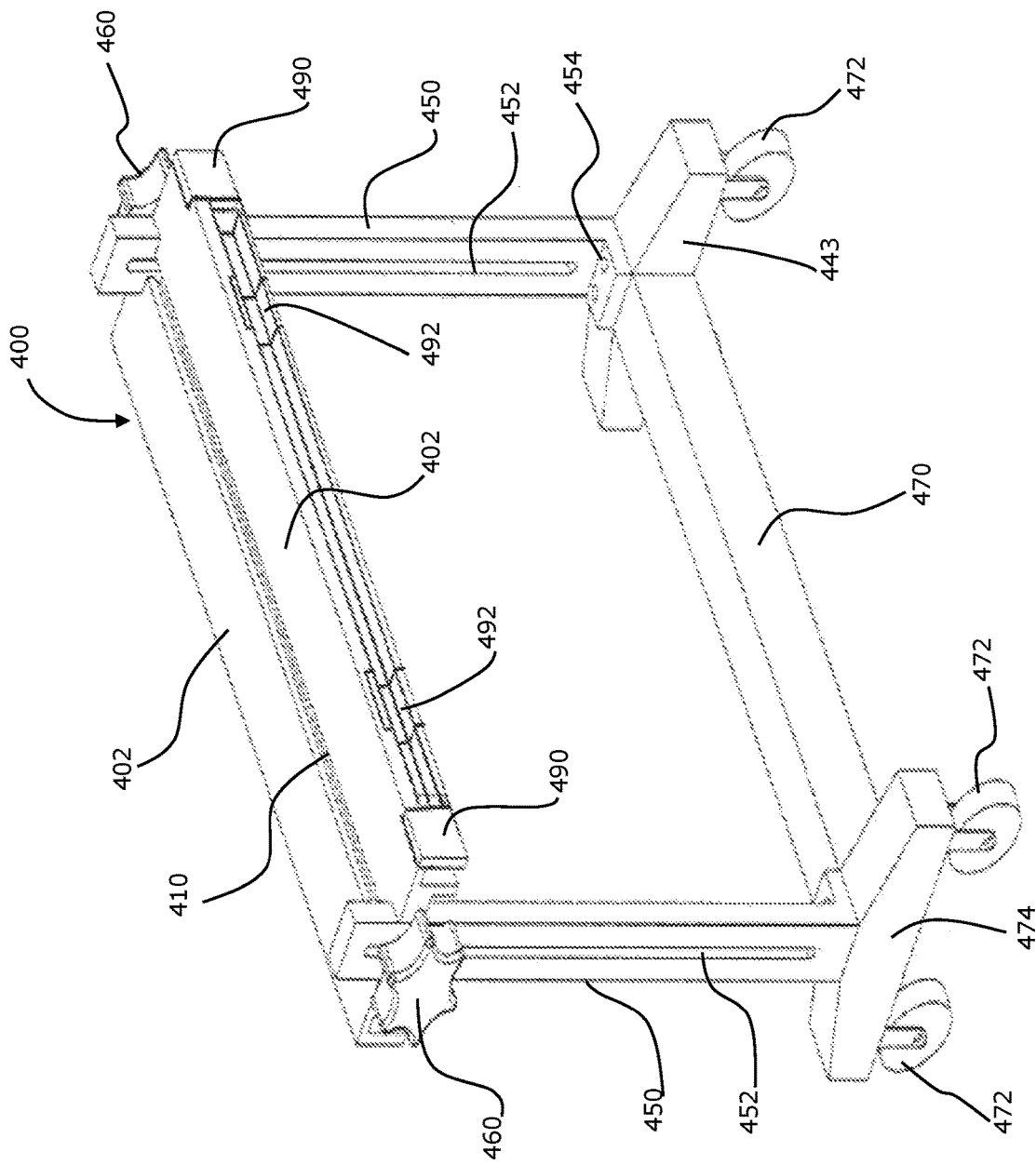
FIG. 16 is a perspective view showing a guide coupled to a wheeled base according to another embodiment of the present invention.

In some configurations, as illustrated by FIGS. 14 and 16, the guide 400 is supported by a pair of height-adjustable vertical stands 450 coupled to each longitudinal ends of the guide 400 so that the platform is grounded. The guide 400 is mounted to the vertical stands 450 in a tongue and groove arrangement and locked with a fastening member 460 in the form of a capped screw. It is to be appreciated that the vertical height of the guide 400 should be about the same height as the height of the operating table 110, and can be adjusted by loosening the fastening member 460, adjusting the guide 400 to a desirable height (for example, parallel to the operating table 110), and locking the vertical position of the guide 400 by tightening the fastening member 460. A mounting end 454 of the stands 450 joins to a base 470 having wheels 472 for ease of relocating the guide 400 before and after coupling with the operating table 110. Advantageously, this configuration allows the guide 400 to be readily detached and moved away from the operating table 110 so that a surgeon is allowed unhindered access to the operating table 110 when manual intervention is necessary. In contrast, conventional robotic arms attached to an operating table are often large and cumbersome and therefore difficult and time-consuming to remove, which can be a major drawback for the patient and the surgeon during surgery.

In a further embodiment, the guide 400 is not coupled to the operating table 110, rather, it is mounted to a freestanding frame with a wheeled base, and positioned proximate a side of the operating table 110.

Figure 15:
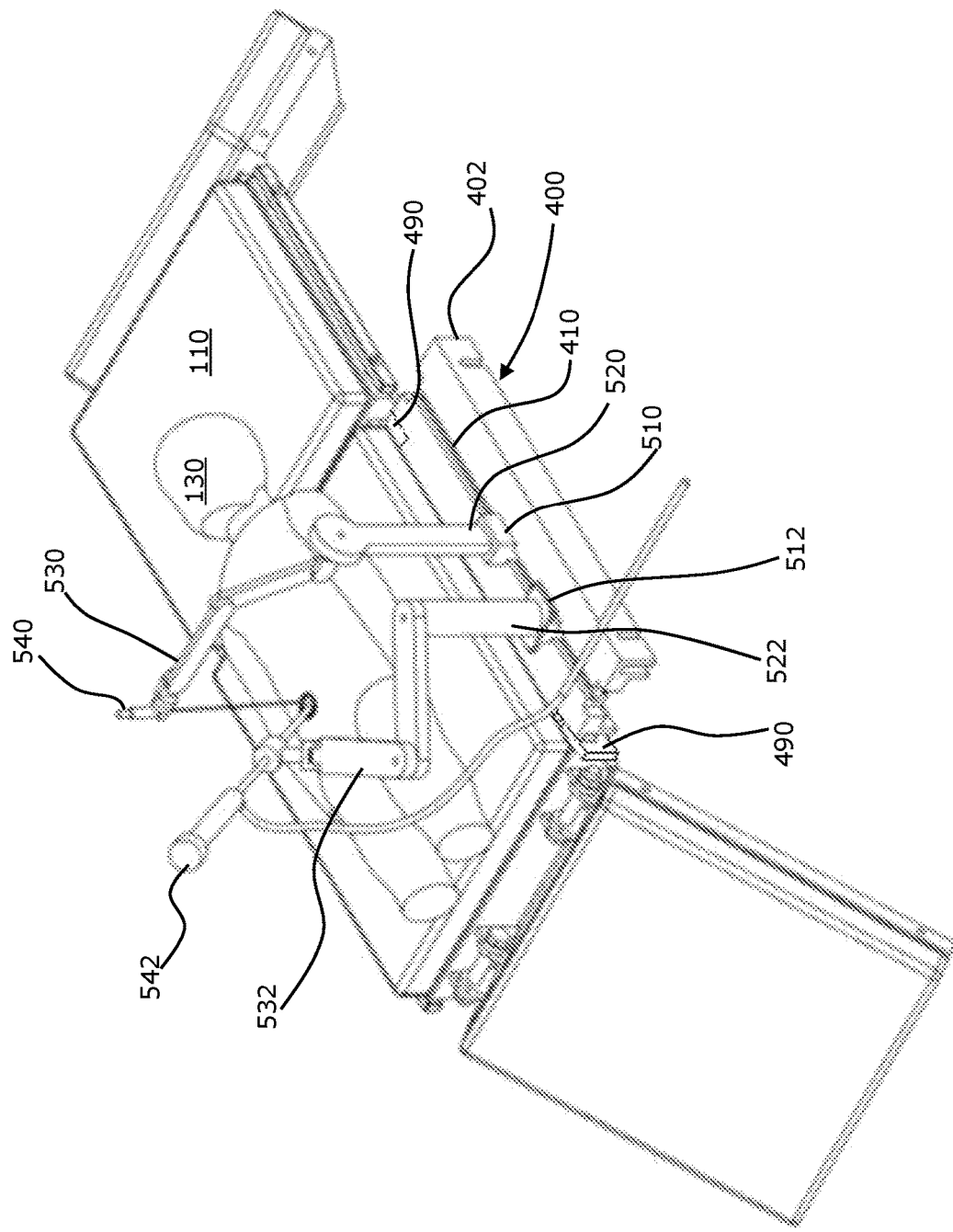
FIG. 15 is a perspective view showing a guide coupled to an operating table according to another embodiment of the present invention.

Returning to FIG. 12, in one embodiment, the guide 400 comprises one or more tracks 410 extending longitudinally along the guide 400. The track 410 is in the form of a groove configuration and suitable for receiving an instrument carrier (either directly, or via a mounting carriage coupled to an instrument carrier) configured to move along the track 410. It is to be understood that the track 410 is not only configured to support an instrument carrier 200 as described above, but can also be configured to support other instrument carriers such as conventional remote centre of motion devices and surgical robotic arms 530, 532 as shown in FIG. 15. In another embodiment, the track 410 is in the form of a rail track having one or more protruding rail guides. In some configurations the track 410 is fitted with drivers, such as for example one or more motorised wheels (not shown), for engaging and moving an instrument carrier along the track 410, and thereby effecting the movement of any surgical instrument 370 mounted to the carrier. The motorised wheel can be controlled remotely by a controller and form part of a robotic surgical system.

An instrument carrier 200 as described above can be movably coupled to the guide 400 (and movable along the track 410) via a supporting carriage 420. The supporting carriage 420 comprises a housing member 422 having a central cavity, which is operatively coupled to the track 22 so that it can move horizontally along the track 410. A shaft 430 is provide to be received within the central cavity of the housing member 422 and is configured to be vertically movable relative to the housing member 422. The mounting member 440, which is coupled to the mounting end 212 of the instrument carrier 200 in use, is further mounted to the top end of the shaft 430 and configured to be rotationally movable relative to the shaft 430. The housing member 422, the shaft 430 and the mounting member 440 can be individually moved by manual force. In one embodiment, the housing member 422, the shaft 430 and the mounting member 440 are individually fitted with drivers, such as for example one or more motorised wheels (not shown), for moving the respective structures, and thereby effecting the movement of any surgical instrument 370 mounted to the carrier 200. The motorised wheel can be controlled remotely by a controller and form part of a robotic surgical system.

Returning now to FIGS. 3 and 4 showing the surgical system; in use, the instrument carrier 200 is as mounted to the support carriage 420 as described above and is capable of horizontal movement (due to movement along the length of the track 410), vertical movement (due to the movement of the shaft 430) and rolling movement (due to rotational movement of the mounting member 440—hence it executes a "swinging" motion). It is to be appreciated that the range of horizontal, vertical and rolling movement adjustments of the instrument carrier 200 allow the instrument carrier 200 and any coupled carriages 300 to move freely without collision. The instrument carriage 300 is operatively coupled to the rail 210, 220 of the instrument carrier 200, and capable of movement along carrier 200 along an arcuate path. A suitable surgical instrument 370, such as an endoscopic or a laparoscopic instrument or tool, is operatively coupled to the support 330 of the instrument carriage 300, which is further capable of omni-directional motion. It can be appreciated that the surgical system described above would assists with the positioning of the coupled surgical instrument during surgery, and advantageously allows the coupled surgical instrument a wide range of motion relative to the operating table 110 and a patient 130 or a suitable target region/subject in respect of the operating table 110. In particular, the arcuate nature of the carrier 200 allows greater flexibility for re-positioning the end portion 374 of the coupled instrument 370 with respect to a patient 130 without the need for large positional adjustments. This advantage makes the present system especially suitable for performing surgical procedures on patients with small bodies, such as children and toddlers in the field of paediatric surgery.

Furthermore, each moving unit of the present invention can be motorised by drivers as described above and form part of a robotic or mechanised surgical system. As used herein, the term 'driver' or 'drivers' include non-limiting examples of mechanical, pneumatic, hydraulic or motorised power movers, such that the subject is actuator driven or driven by means of motorised movement. Each of the drivers is connected to a controller, via wired or wireless connection. The controller is configured to receive directional input for an end point of the surgical instrument. The controller is configured to compute corresponding movement required by the drivers to replicate the moment of the end point of the surgical instrument in response to the directional input, and provide output signals to actuate the drivers based on the directional input.

It is to be appreciated that the above described robotic surgical system could work as part of a master-slave robot configuration where all the motorised components are part of a "slave-network" that could be controlled by a remote, "master" controller. The motorised "master" manipulation of the instrument can be carried out by omni-directional motion of the tool capture unit at the end-effectors about a distal pivot point, commonly referred to as the Remote Centre of Motion (RCM), under surgeon's supervision. Master controls can be configured with fingertip control, motion scaling and tremor reduction for precise surgical interventions such as suturing, dissection and tissue manipulation. A controller is provided to receive RCM directional input from a surgeon using a remote control unit for the end portion 374 of the coupled surgical instrument 370. The controller is configured to determine a corresponding movement of the instrument 370 required, and provide output signals to actuate the drivers (such as motorised wheels) of the instrument carrier 200, carriage 300, housing member 422, the shaft 430 and the mounting member 440 based on the input to achieve a corresponding positioning of the instrument 370 as required. Motorised control of the above described system also provides improved accuracy and stability of the coupled instrument 370 in comparison to conventional surgical instrument carriers (such as anthropometric robotic arms) as re-positioning movement of the coupled instrument 370 is reduced with the present system. The arcuate rail 210, 220 also advantageously allow the surgical instrument to travel along an arcuate path relative to the patient or the target region, further minimising required movement of the coupled instruments. The present system is also more flexible and cost-effective to configure. For example, a plurality of instrument carriages 300 may be added to each of the carriers 200, thereby avoiding the need for a new robotic arm to be installed for each additional surgical instrument, rather, a surgeon would only need to add an additional instrument carriage 300 to the system.

It is to be appreciated that the arcuate rail 210, 220 provides the following additional advantages: (1) better registration of surgical instruments to the surgical active area and/or target regions; (2) positioning surgical instruments, movably mounted on the arcuate rail 210, 220, in close vicinity to the target region; and (3) providing flexible and safer motion trajectories of the instruments in coordinating with additional instruments movably mounted on other arcuate rails 210, 220.

In particular, three robotic system configurations using the present system is described below using the instrument carriers 200 as bases for RCM mechanism for maximum achievable accuracy. The motorised quadrant carriers 200 and semi-circular carriers 200 envelop the patient or target region. The coupled instruments 370 as supported by the carriage 300 mounted on the carriers 200 are able to move over the rails 210, 220 on either side of the operating table 110, move vertically at a given horizontal position and rotate sideways (yaw) at a given height. The horizontal, vertical and rotational movements are used to coarsely localise (register) the closest convenient position over the patient or target region for aiming at a target location. First system configuration: semi-circular carrier 200 only as shown in FIG. 4 is suitable for carrying bulky tools/instruments at relatively constant position (less variable payloads)—equipment/instruments/tools such as the endoscope, insufflation/irrigation tools etc. Second system configuration: quadrant carriers 200 as shown in FIG. 3 is suitable for carrying lighter weight equipment/instruments/tools required for relatively frequently moveable payloads such as surgical instruments. Third system configuration: a hybrid configuration of one semi-circular and two quadrant carriers 200 together allows enhanced manoeuvrability of the tools and surgical instruments during surgery.

The disclosed robotic surgical platform would have various clinical benefits such as improved dexterous manoeuvrability of the coupled instruments and better reach for paediatric patients by using an instrument support 330 that is capable of carrying 3 mm and 5 mm diameter instruments for working through constrained workspaces and critical anatomical structures. The present system allows more complex operative procedures to be performed on both paediatric and neonatal patient as this group of patients would benefit from the advantages of the present system which could position surgical instruments in spatially constrained operative workspaces. Potential paediatric subspecialty applications of this system include paediatric general surgery, thoracic surgery, paediatric urology, and both paediatric and adult neurosurgery and ENT. The ability to use 3 mm and 5 mm endoscopic instrumentation such as high-energy vessel sealing technology and other innovative instruments is highly beneficial. Other relevant clinical applications for this system include laparoscopy; flexible endoscopy; microsurgery; general surgery; urology; gynaecology; tubal ligation using fetus scope and prostate resection.

Although the instrument carrier 200 and the robotic system has been described as preferably designed for small patients, high accuracy and stability in mind, it is to be appreciated that there is no limitation on scalability to extend it to adult patients and/or patients of any anthropometric domains.

Referring to FIG. 15, the guide 400 as described above can also be configured to support payloads in the form of conventional surgical instrument carriers 530, 532 (such as robotic arms). FIG. 15 shows two examples of robotic arm type instrument carriers mounted to respective carriages 520, 522, which are movable horizontally along the track 410. The guide 400 as shown in FIG. 15 has a horizontal plate with a slotted rail track 410. This rail holds a carriage 520, 522 which traverses the rail track 410 by actuated or manual means. Two standard surgical tools 540, 542 are mounted to the guide 400 via industrial arm robots: these are a laparoscopic tool and a flexible endoscope. The guide 400 can be mounted to a standard operating table 110 similarly as described previously, by an electromagnetic latch 492 and a mechanical lock 490. The electromagnetic latch 492 is activated when a current is applied, and attracts the guide to the operating table 110. The mechanical lock 490 consists of a sliding plate which slots in behind a horizontal rail track 410 on the table to make a more stable mechanical connection. By the combination of these two connections, a reliable reference position can be achieved for any robotic arms on the guide 400.

FIG. 16 shows a portable frame which supports the guide 400 assembly. The guide 400 is connected to the frame by height adjustable screws in a vertical stand 450. This adjustable connection allows the rail assembly to be fixed at different heights for adjustable height tables or when consecutively using the guide on tables of different fixed heights. The height adjustable stand 450 connects to a wheeled base 470 which consists of a rigid frame and caster wheels 472, allowing the frame and guide 400 assembly to be removed from the table easily, once the electromagnetic latch 492 and mechanical lock 490 are disengaged. The ability to disengage the frame from the table is a safety feature such that in the event of any unintended consequence of robotic surgery, it is required to disengage the system/patient as urgency situation and/or to partially take-over the surgery by manual means due to any preferred situation—the system is made to be capable of shutdown and disengage in minimum possible time to give complete access to the surgeons for manual access to the patient.

In a clinical setting, the guide 400 assembly can be mounted to the operating table 110. The guide assembly can then be used to mount different surgical tools, such as the robotically guided laparoscopic tool shown in FIG. 15, via a movable carriage 510, 512. This provides both a mechanical support for the arm, and a reference point which will not move relative to the patient, because the guide assembly is securely connected to the table by the electromagnetic latch 492 and mechanical lock 490. Prior to treatment or diagnostics, the carriages 510, 512 can be positioned by motors, and locked in place. At any point before treatment, the height adjustment screws 460 can be released to allow the guide 400 to follow any required height adjustment of the operating table 110, and then tightened to lock the guide assembly at a given height above the floor. Once height adjustment and carriages are locked in place, and guide 400 assembly is rigidly connected to the table, the arms 530, 532 can be used to perform a variety of clinical tasks. An identical guide 400 assembly can be placed adjacent the existing rail or on the opposite side of the table 110, accommodating more carriages and instruments with the ability to reach different regions.

Figure 17:
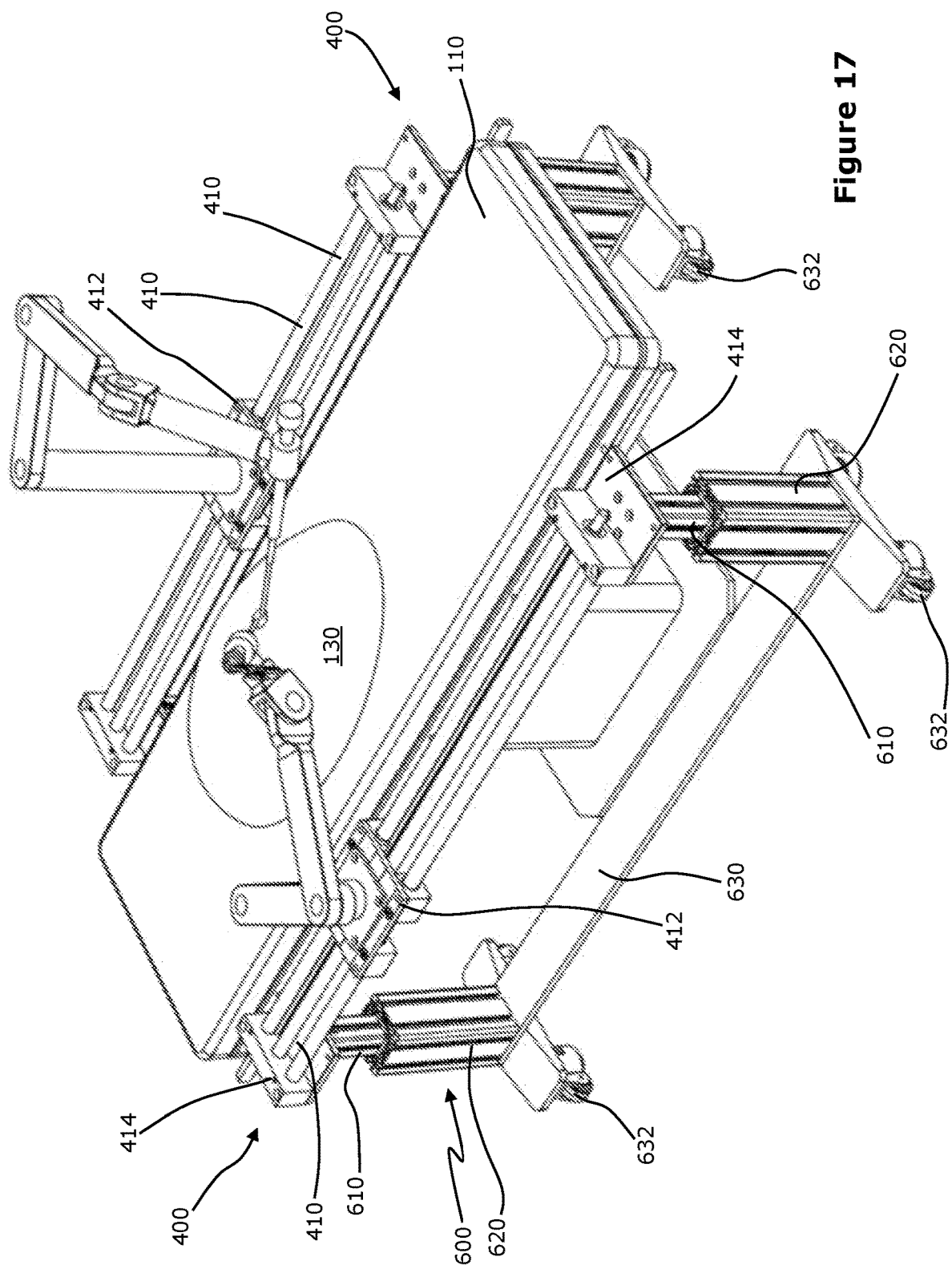
FIG. 17 is a perspective view showing guides of a further embodiment of the present invention mounted to a support frames and coupled to an operating table.
Figure 18:
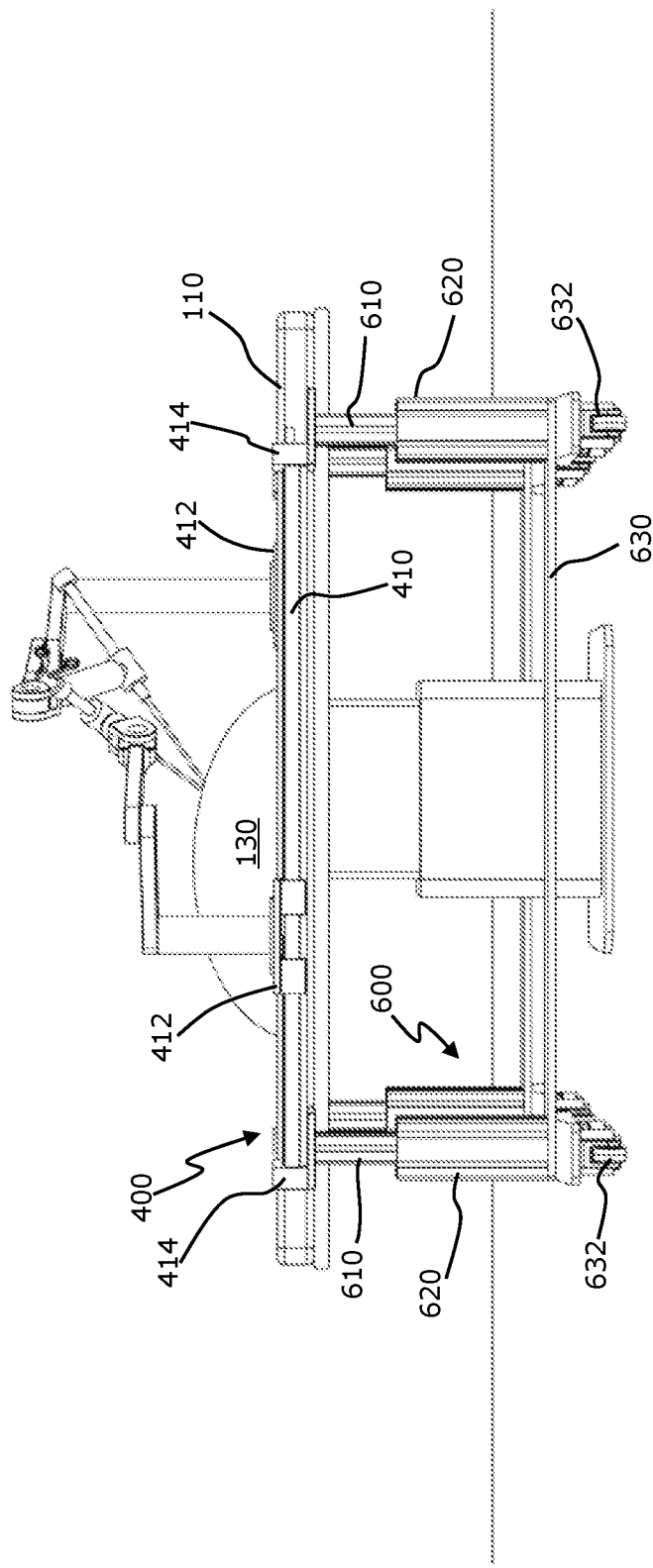
FIG. 18 is a front view of the guides and the operating table of FIG. 17.
Figure 19:
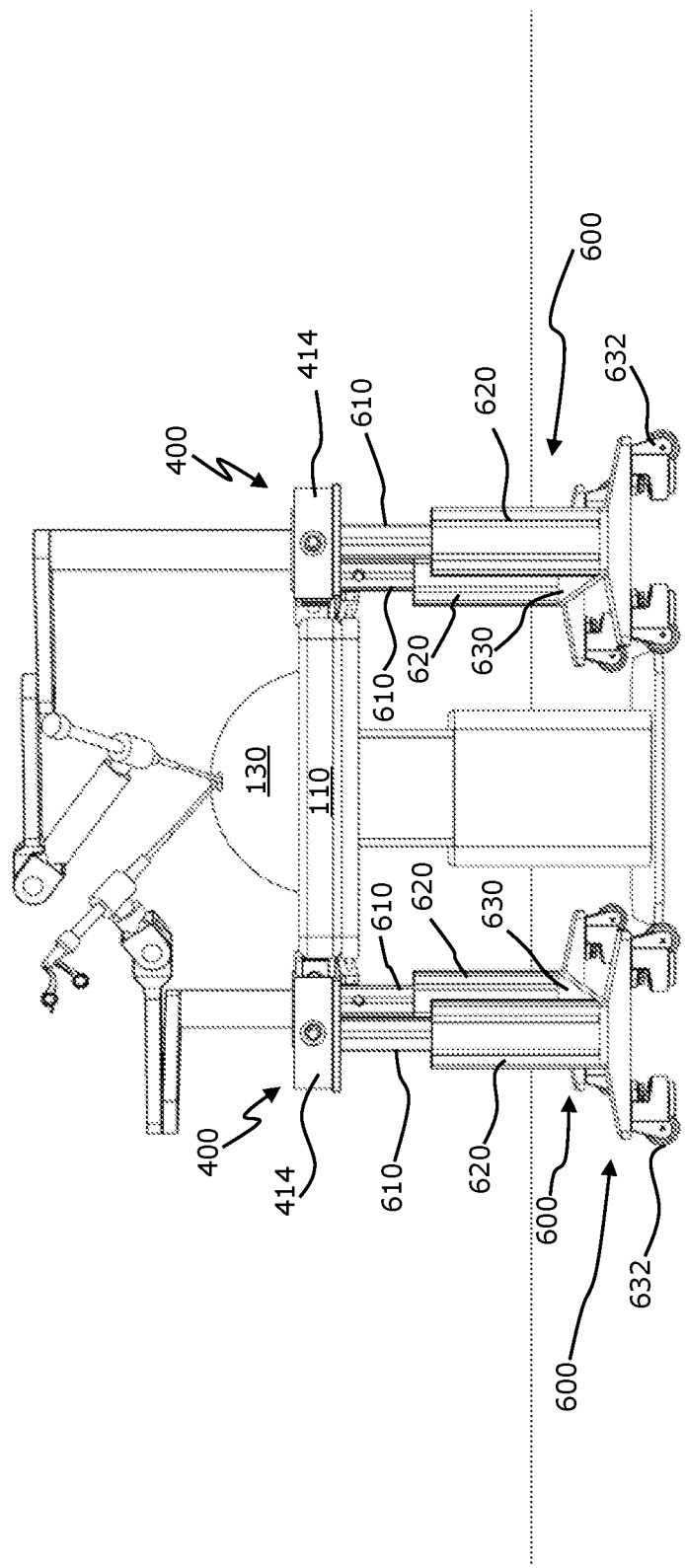
FIG. 19 is a side view of the guides and the operating table of FIG. 18.

FIGS. 17 to 19 illustrate a further embodiment of the present invention in which guides 400 are supported on portable support frames 600 for use with any other suitable surgical or robotic installations. In this embodiment, each guide 400 comprises one or more longitudinal track(s) 410 which run alongside an operating table 110 during use and the track(s) 410 are configured for receiving a moveable platform 412. The longitudinal track 410 can be defined by one or more suitably configured beams or rods positioned between supports 414 located at opposing ends of the guide 400 and the platform 412 is configured with corresponding grooves or cavities for interfacing with the track 410. It is to be understood that the platform 412 can be used as a base to mount any suitable surgical or robotic installations such as one or more robotic arms of the same or variable mechanical configurations as suited to the required surgical actions. In this embodiment, the guide 400 is mounted to the portable support frames 600 by coupling the supports 414 located at opposing ends of the guide 400 to corresponding stands 610.

The stands 610 are telescopically receivable by corresponding legs 620 which are connected by a base 630. The support frame 600 is configured with wheels 632 for mobility of the frame 600 and guide 400 when it is coupled to the frame 600 for ease of attachment and detachment during emergency situations or preferred manual uptake of whole or part of the procedure. Like guide 400 and support frame 600 can be positioned on opposing sides of the operating table 110. It can be appreciated that mounting robotic systems on one or more moveable platforms 412 would enhance the range of motion and action available to the robotic systems with respect to a patient 130 while keeping a safe distance from the patient 130 and expanding robot-to-robot collaborative functionality; therefore expanding the type and nature of surgical applications/activities available. It is considered that robotic systems used this way could reach the patient by re-orientating the degrees of freedom at different angles of a robotic arm without compromising the distance to the patient and/or undue forces on patients' anatomy. The number of robotic arms used and mechanical configurations would depend on the surgical task. Non-limiting examples of the robotic arms include surgical robotic arms, scrub nurse systems and passive clamp systems.

Further, it is to be understood that the guide is not only configured for use for carrying medical or surgical payloads such as instrument carriers, but it is equally suitable for use with work surfaces in the field of industrial automation and manufacturing plants, such as for example automotive assembly conveyor lines. Instrument carriers in the field of industrial automation and manufacturing plants could include non-limiting examples, such as assembly and industrial robotics.

It will be understood that the invention disclosed and defined in this specification extends to all alternative combinations of two or more of the individual features mentioned or evident from the text or drawings. All of these different combinations constitute various alternative aspects of the invention.

In the description and drawings of this embodiment, same reference numerals are used as have been used in respect of the first embodiment, to denote and refer to corresponding features.

While various embodiments of the present invention have been described above, it should be understood that they have been presented by way of example only, and not by way of limitation. It will be apparent to a person skilled in the relevant art that various changes in form and detail can be made therein without departing from the spirit and scope of the invention. Thus, the present invention should not be limited by any of the above described exemplary embodiments.

The invention claimed is:

1. An instrument carrier for assisting with the positioning of a surgical instrument during surgery, comprising:
an arcuate rail mountable at a mounting end to an operating table and moveable relative to the table for positioning the rail over a target region in use, the arcuate rail being further configured for rolling movement in a direction perpendicular to the rail by rotating about the mounting end; and
a carriage operatively coupled to the rail, the carriage having a support for carrying the surgical instrument, the support comprising a ball joint having a cavity central to the ball of the joint in which a shaft for receiving the surgical instrument is movable, and a rack and pinion drive for moving the shaft;
wherein the carriage is configured to be movable along the rail such that movement of the carriage positions the surgical instrument along an arcuate path relative to the target region.

2. An instrument carrier as claimed in claim 1, wherein the rail is motorized to pivot relative to the table about a mounting end of the rail, and the carriage is motorized to move along the rail.

3. An instrument carrier as claimed in claim 2, wherein movement of the carrier and the instrument is remotely controlled.

4. An instrument carrier as claimed in claim 1, wherein the support is configured to receive surgical instruments having a diameter of 5 mm or less.

5. An instrument carrier as claimed in claim 1, wherein the rail extends substantially only half way across a width of an operating table.

6. An instrument carrier as claimed in claim 5, wherein the carrier is adapted to be joined to an opposing like carrier to form a unitary rail which extends across substantially the entire width of an operating table.

7. An instrument carrier as claimed in claim 1, wherein the rail extends across substantially the entire width of an operating table.

8. An instrument carrier as claimed in claim 1, wherein the support is adapted to carry an endoscopic or laparoscopic instrument.

9. An apparatus for use in supporting an instrument as claimed in claim 1, comprising a guide mountable to a work surface such that it extends along a side of the work surface in use, the guide comprises one or more tracks extending in a longitudinal direction and adapted for supporting and moving the instrument carrier along the track.

10. An instrument carrier as claimed in claim 1, further comprising a second arcuate rail, wherein one of the rails is in the form of a semi-circle, and the other rail is in the form of a quadrant of a circle.

11. An apparatus for use in supporting an instrument carrier as claimed in claim 10, comprising a guide mountable to a work surface such that it extends along a side of the work surface in use, the guide comprises one or more tracks extending in a longitudinal direction and adapted for supporting and moving the instrument carrier along the track.

12. An instrument carrier for assisting with the positioning of a surgical instrument during surgery, comprising:
an arcuate rail mountable at a mounting end to an operating table to extend substantially only half way across a width thereof, and moveable relative to the table for positioning the rail over a target region in use, the arcuate rail being further configured for rolling movement in a direction perpendicular to the rail by rotating about the mounting end; and
a carriage operatively coupled to the rail, the carriage having a support for carrying the surgical instrument;
wherein the carriage is configured to be movable along the rail such that movement of the carriage positions the surgical instrument along an arcuate path relative to the target region,
wherein the carrier is adapted to be joined to an opposing like carrier to form a unitary rail which extends across substantially the entire width of the operating table, and
wherein the support comprises a ball joint having a cavity central to the ball of the joint for receiving a surgical instrument.

13. An instrument carrier as claimed in claim 12, wherein a shaft for receiving a surgical instrument is axially located within the ball joint and movable relative to the ball joint, the central cavity having a rack and pinion drive for moving the shaft.

* * * * *